United States Patent
Trzasko et al.

(10) Patent No.: US 10,769,820 B2
(45) Date of Patent: Sep. 8, 2020

(54) SYSTEM AND METHOD FOR MODEL-BASED RECONSTRUCTION OF QUANTITATIVE IMAGES

(71) Applicant: MAYO FOUNDATION FOR MEDICAL EDUCATION AND RESEARCH, Rochester, MN (US)

(72) Inventors: Joshua D. Trzasko, Rochester, MN (US); Armando Manduca, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/032,938

(22) PCT Filed: Oct. 22, 2014

(86) PCT No.: PCT/US2014/061688
§ 371 (c)(1),
(2) Date: Apr. 28, 2016

(87) PCT Pub. No.: WO2015/065781
PCT Pub. Date: May 7, 2015

(65) Prior Publication Data
US 2016/0253825 A1    Sep. 1, 2016

Related U.S. Application Data

(60) Provisional application No. 61/897,297, filed on Oct. 30, 2013.

(51) Int. Cl.
*G06T 11/00* (2006.01)
*G06T 7/00* (2017.01)
(Continued)

(52) U.S. Cl.
CPC ............ *G06T 11/003* (2013.01); *A61B 5/743* (2013.01); *G01R 33/5608* (2013.01);
(Continued)

(58) Field of Classification Search
None
See application file for complete search history.

(56) References Cited

U.S. PATENT DOCUMENTS

| | | |
|---|---|---|
| 7,657,299 B2 * | 2/2010 | Huizenga ............... A61B 5/055 382/276 |
| 7,667,298 B2 | 2/2010 | Huizenga et al. |

(Continued)

OTHER PUBLICATIONS

Ramani, Sathish, and Jeffrey A. Fessler. "Regularized parallel MRI reconstruction using an alternating direction method of multipliers." Biomedical Imaging: From Nano to Macro, 2011 IEEE International Symposium on. IEEE, 2011.*

Ramani, Sathish, and Jeffrey A. Fessler. "Parallel MR image reconstruction using augmented Lagrangian methods." IEEE Transactions on Medical Imaging 30.3 (2011): 694-706.*

(Continued)

*Primary Examiner* — Vu Le
*Assistant Examiner* — Tracy Mangialaschi
(74) *Attorney, Agent, or Firm* — Quarles & Brady LLP

(57) ABSTRACT

A system and method for estimating a physiological parameter from data acquired with a medical imaging system includes acquiring data with the medical imaging system. A physiological parameter is estimated from the acquired data using an iterative estimation in which a model of the medical imaging system is decoupled from a physics-based model of the acquired data.

20 Claims, 2 Drawing Sheets

(51) Int. Cl.
*A61B 5/00* (2006.01)
*G01R 33/56* (2006.01)
(52) U.S. Cl.
CPC .......... *G06T 7/0012* (2013.01); *G06T 7/0016* (2013.01); *G06T 2207/10076* (2013.01); *G06T 2207/10088* (2013.01); *G06T 2207/10092* (2013.01)

(56) References Cited

U.S. PATENT DOCUMENTS

| | | | |
|---|---|---|---|
| 8,031,927 | B2 | 10/2011 | Karl et al. |
| 8,175,355 | B2 | 5/2012 | El Fakhri et al. |
| 2011/0044524 | A1* | 2/2011 | Wang ............ G01R 33/54 382/131 |
| 2013/0182930 | A1 | 7/2013 | Trzasko et al. |
| 2013/0214781 | A1* | 8/2013 | Hernando .......... G01R 33/4828 324/309 |
| 2013/0343625 | A1* | 12/2013 | Samsonov ........... G06T 11/005 382/131 |

OTHER PUBLICATIONS

Zhao, Bo, et al. "Image reconstruction from highly undersampled (k, t)-space data with joint partial separability and sparsity constraints." IEEE transactions on medical imaging 31.9 (2012): 1809-1820.*

Trzasko, Joshua D., et al. "Estimating T1 from multichannel variable flip angle SPGR sequences." Magnetic resonance in medicine 69.6 (Published online Jul. 17, 2012 in Wiley Online Library): 1787-1794.*

Xu, Wenlong, Xiaofang Liu, and Xia Li. "Sparse Constrained Reconstruction for Accelerating Parallel Imaging Based on Variable Splitting Method." Computational and mathematical methods in medicine 2013; 2013:605632. doi: 10.1155/2013/605632. Epub Mar. 31, 2013.*

Weller DS, Ramani S, Fessler JA. Augmented Lagrangian with Variable Splitting for Faster Non-Cartesian L1-SPIRiT MR Image Reconstruction. IEEE transactions on medical imaging. Oct. 9, 2013;33(2). (Year: 2013).*

International Search Report and Written Opinion dated Feb. 5, 2015 in connection with PCT/US2014/061688.

* cited by examiner

US 10,769,820 B2

SYSTEM AND METHOD FOR MODEL-BASED RECONSTRUCTION OF QUANTITATIVE IMAGES

CROSS-REFERENCE TO RELATED APPLICATIONS

This application represents the national stage entry of PCT International Application No. PCT/US2014/061688 filed Oct. 22, 2014, which claims priority to, U.S. Provisional Application Ser. No. 61/897,297, filed Oct. 30, 2013, both of which are hereby incorporated herein by reference for all purposes.

STATEMENT REGARDING FEDERALLY SPONSORED RESEARCH

N/A

BACKGROUND

The field of the disclosure relates to systems and methods for medical imaging. More particularly, the disclosure relates to systems and methods for creating quantitative images from images that inherently lack or lack complete quantitative information, such a magnetic resonance imaging ("MRI") images.

Quantitative MRI applications typically involve the acquisition of a series of images, from which physiological parameters are estimated by fitting information in the images to physics-based models. Common examples of quantitative MRI applications include diffusion imaging, perfusion imaging, relaxometry, and elastography. Unlike imaging modalities such as digital photography, images are not directly observed in MRI. Rather, samples of spatial-spectral transformations of the images-of-interest are collected. MRI data is also routinely collected using phased-array (i.e., multi-channel) receivers. For these reasons, the estimation of physiological parameters in model-based MRI is a challenging inverse problem.

In the abstract, the problem of estimating physiological parameters from physics-based signal models in an accelerated MRI framework corresponds to performing a high-dimensional, penalized non-linear least squares ("NLLS") regression. Although classic "black box" numerical solvers like the Levenberg-Marquardt NLLS iterative routine can be applied for such problems, they are notoriously inefficient and numerically sensitive/unstable. Moreover, since such classic methods are inherently gradient-based (in the sense that they operate by directly marching down the cost functional in the direction of its negative local gradient), they operate poorly for problems where the signal model is not bijective, such as for any phase-based quantitative MRI application that may exhibit "wrapping."

It would therefore be desirable to provide systems and methods for providing clinicians with quantitative information, despite needing to use imaging modalities that inherently lack or lack complete quantitative information.

SUMMARY

The present disclosure overcomes the aforementioned drawbacks by providing systems and methods for estimating a physiological parameter from data acquired with a medical imaging system, such as a magnetic resonance imaging ("MRI") system. Data is acquired with the medical imaging system, from which a physiological parameter is estimated using an iterative estimation in which a model of the medical imaging system is decoupled from a physics-based model of the acquired data. The model of the medical imaging system may be, for example, a large-scale system operator that describes the acquisition of data using the medical imaging system. In the context of MRI, this model may include a Fourier transform. In the context of MRI, the physics-based model of the acquired data may include a magnetic resonance signal model.

In accordance with one aspect of the disclosure, a system for generating medical images is disclosed that includes a communications connection configured to receive image data acquired from a subject using a medical imaging system. The system also includes a processor configured to receive the image data. The processor is further configured to estimate a physiological parameter from the image data using a model of the medical imaging system is decoupled from a physics-based model of the image data and iteratively minimize a cost function that includes the model of the medical imaging system and the physics-based model of the acquired data to quantify the physiological parameter of the subject from the image data. The processor is also configured to reconstruct a set of medical images of the subject from the image data at least including the physiological parameter of the subject.

In accordance with another aspect of the disclosure, a method is provided for estimating a physiological parameter from data acquired with a medical imaging system. The method includes acquiring data with the medical imaging system and estimating a physiological parameter from the acquired data using an iterative estimation in which a model of the medical imaging system is decoupled from a physics-based model of the acquired data.

In accordance with yet another aspect of the disclosure, a magnetic resonance imaging (MRI) system is provided that includes a magnet system configured to generate a polarizing magnetic field about at least a portion of a subject arranged in the MRI system and a magnetic gradient system including a plurality of magnetic gradient coils configured to apply at least one magnetic gradient field to the polarizing magnetic field. The MRI system also includes a radio frequency (RF) system configured to apply an RF field to the subject and to receive magnetic resonance signals from the subject using a coil array and a computer system. The computer system is programmed to control the magnetic gradient system and the RF system to acquire image data and estimate a physiological parameter from the image data using an iterative estimation in which a model of the MRI system is decoupled from a physics-based model of the image data.

The foregoing and other aspects and advantages will appear from the following description. In the description, reference is made to the accompanying drawings which form a part hereof, and in which various examples are shown by way of illustration. Any embodiments do not necessarily represent the full scope of the invention, however, and reference is made therefore to the claims and herein for interpreting the scope of the invention.

DETAILED DESCRIPTION

Described here are systems and methods for that provide a numerical strategy for reconstructing images from limited amounts of data, such as reconstructing images from magnetic resonance imaging ("MRI") data acquired using an accelerated data acquisition that undersamples k-space. Although some aspect of the present disclosure will discuss an application for quantitative MRI, the systems and methods described herein can be applied to other technological areas both within and outside of medical imaging.

MRI is widely used to diagnostically investigate the human body. However, unlike other medical imaging modalities (e.g., x-ray computed tomography), MRI data is not explicitly quantitative. That is, pixel values do not directly represent physiological information. There is strong clinical interest in transforming MRI into a quantitative modality, and to measure quantities such as flow, diffusion, perfusion, T1 relaxation times, and fat/water concentrations. For these applications, series of images are collected (e.g., at different acquisition settings), the acquired data is fit to physics-based models, and relevant physiological parameters are extracted. During this process, however, MRI data typically passes through a complex processing pipeline. Although errors in raw MRI data are well-understood, how they propagate through such a pipeline is not, and current results on these applications are typically biased and error-prone.

The systems and methods of the present disclosure overcome these drawbacks by providing a generally applicable framework that directly can be used to estimate physiological parameters from the acquired imaging data, even if this data is incomplete (i.e., "undersampled"), thereby enabling statistically optimal error handling and increased accuracy. Given the strong statistical motivation behind this framework, as well as robust handling of challenging mathematical issues like signal bias and non-uniqueness, it is contemplated that the systems and methods described here will facilitate bringing quantitative MRI techniques into routine clinical use. This framework, and the computational methods that practically apply it, is a significant advance towards making MRI a clinically-useful quantitative diagnostic tool.

Figure 1:
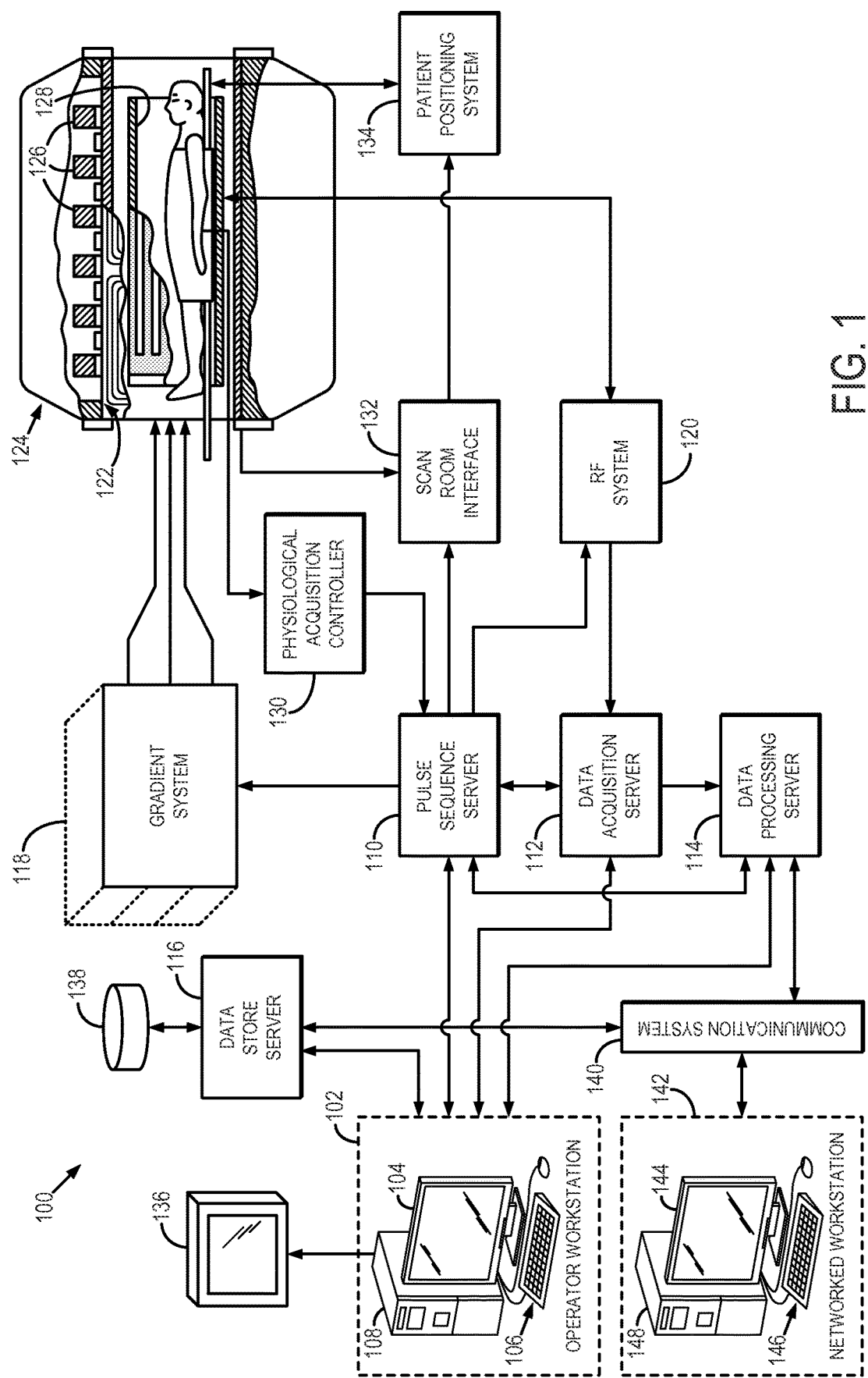
FIG. 1 is a block diagram of an example of a magnetic resonance imaging ("MRI") system.

As will be described, the systems and methods of the present disclosure may be used with a variety of different imaging modalities. As one non-limiting example, a magnetic resonance imaging ("MRI") system will be described. Referring particularly now to FIG. 1, an example of an MRI system 100 is illustrated. The MRI system 100 includes an operator workstation 102, which will typically include a display 104; one or more input devices 106, such as a keyboard and mouse; and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. To this end, the operator workstation 102 (or, as will be described, other workstations 142) are connected to receive data acquired by the MRI system 100. For example, the servers 110, 112, 114, and 116 may be connected via a communication system 140, which may include any suitable network connection, whether wired, wireless, or a combination of both. As an example, the communication system 140 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil (not shown in FIG. 1), are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays (not shown in FIG. 1).

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \qquad (1);$$

and the phase of the received magnetic resonance signal may also be determined according to the following relationship:

$$\varphi = \tan^{-1}\left(\frac{Q}{I}\right). \qquad (2)$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography ("MRA") scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or threedimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

Figure 2:
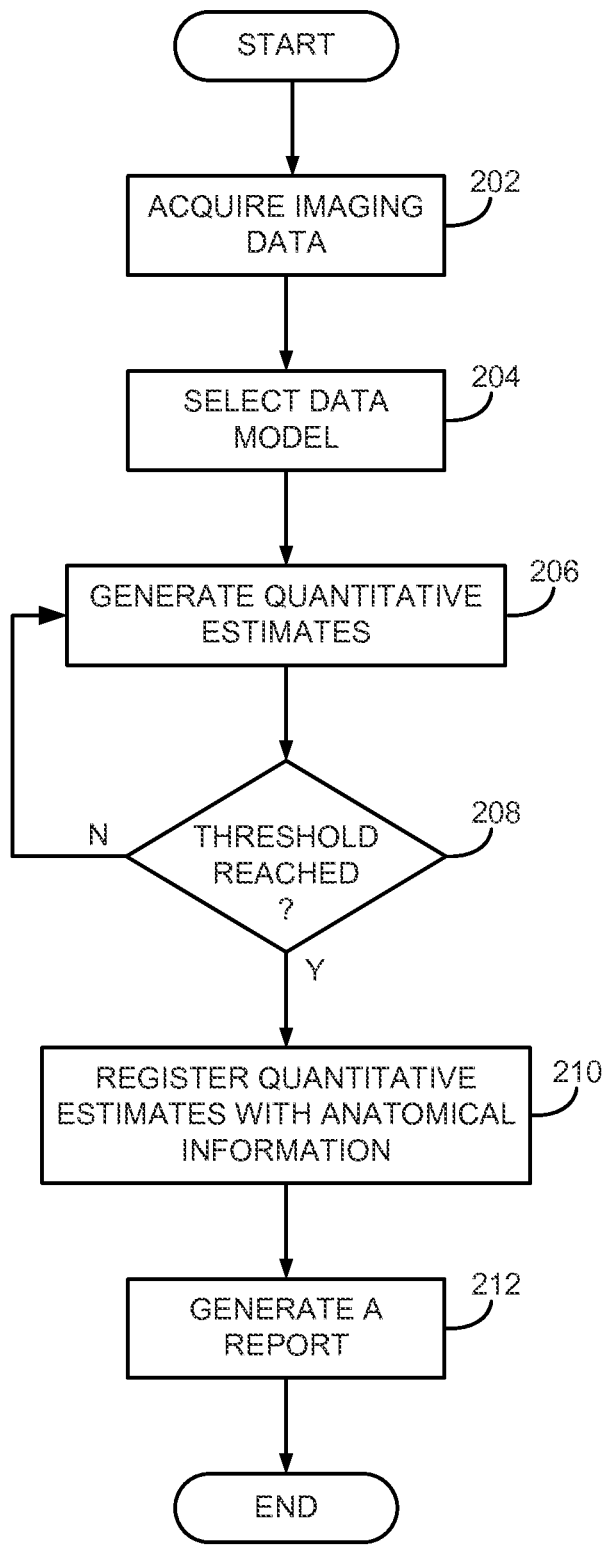
FIG. 2 is a flow chart setting forth examples of steps that may be performed in accordance with the present disclosure.

Referring to FIG. 2, a process 200 in accordance with the present disclosure begins at process block 202 by acquiring medical imaging data. Thereafter, at process block 204, a model for the data is selected. For example, using a medical imaging system, such as the above-described MRI system 100, an MRI signal model is selected. Suppose T imaging studies are performed, with each study corresponding to a different time point or, in the case of an MRI acquisition, a pulse sequence parameterization. During each study or acquisition, the C receiver channels each collect K data samples. This K×T×C data set can be modeled as:

$$g[k,t,c] = \sum_{n=0}^{N-1} A[k,t,c]f[n,c]F_\phi[n,t] + z[k,t,c]; \quad (3)$$

where k is the observed signal sample index; t is the experiment index; c is the receiver channel index; A is a K×N×T spatial-spectral system model; f is an N×C matrix of ancillary parameters; ϕ is an N×1 vector or N×T matrix of physiological parameters of interest; $F_\phi$ is an N×T physics-based signal model; and z is complex Gaussian noise. In magnetic resonance imaging applications, the system model, A, often corresponds to a partial discrete Fourier transform ("DFT") as:

$$A[k,n,t] = e^{-j\vec{x}[n]\cdot\vec{\omega}[k,t]} \quad (4).$$

Additionally, it can be assumed that the corrupting noise process is described by $\Re\{z[k,t,c]\}$, $\Im\{z[k,t,c]\} \square N(0,\sigma^2)$. The ancillary parameters, f, represent quantities that are not of primary interest. In quantitative MRI applications, for example, this may include coil sensitivity profiles used in accelerated imaging studies. As will be shown, as desired, these parameters can be marginalized out of the estimation problem. The physics-based signal model, $F_\phi$, selected at process block 204 can be, for example, either a linear or nonlinear functional. For example, in the case of an MRI data acquisition using a spoiled gradient recalled echo ("SPGR") pulse sequence, $R_1$ relaxometry, ϕ is an N×1 vector representing the relaxation values for different tissues and:

$$F_\phi[n,t] = \sin(\theta[t])\frac{1-e^{-\tau\phi[n]}}{1-\cos(\theta[t])e^{-\tau\phi[n]}}; \quad (5)$$

where θ and τ are pulse sequence parameters.

Thus, parameter estimation can begin. The signal model in Eqn. (3) can be equivalently expressed as a KT×C matrix:

$$g = \begin{bmatrix} A[:,:,0] & 0 & \cdots & 0 \\ 0 & \ddots & \ddots & \vdots \\ \vdots & \ddots & \ddots & 0 \\ 0 & \cdots & 0 & A[:,:,T-1] \end{bmatrix} \begin{bmatrix} \text{diag}(F_\phi[:,0]) \\ \vdots \\ \text{diag}(F_\phi[:,T-1]) \end{bmatrix} f + \quad (6)$$

$$z = AG(\phi)f + z.$$

Because z is Gaussian, maximum likelihood ("ML") estimates of f and ϕ, which are both unknown parameters, are solutions to a separable nonlinear least squares problem. In practice, however, K<N, and the system in Eqn. (6) is underdetermined.

At process block 206, the model selected at process block 204 is used to generate a quantitative estimate. As will be described, estimating quantitative estimates of physiological parameters from the acquired data can be performed using an iterative estimation in which a model of the medical imaging system is decoupled from a physics-based model of the acquired data. More particularly, the process can iteratively minimize a cost functional that includes the model of the medical imaging system and the physics-based model of the acquired data.

In particular, an initial estimate may be derived from the acquired data and, for this estimation to be well-posed, auxiliary regularization or constraints may be used. To this end and continuing with the non-limiting example of MRI data, the following regularized nonlinear least squares model can be employed for physiological parameter estimation in undersampled quantitative MRI:

$$J(f,\phi)=P(\phi)+\|AG(\phi)f-g\|_F^2 \quad (7);$$

where $P(\cdot)$ is a penalty functional, which may not necessarily be smooth, and $\|\cdot\|_F$ denotes the Frobenius matrix norm. Because f is ultimately not of interest, it can be left unregularized.

Consider the special case of Eqn. (7) where A is the identity operator, where:

$$J(f,\phi)=P(\phi)+\|G(\phi)f-g\|_F^2 \quad (8).$$

Although f and ϕ can be jointly estimated using standard optimization strategies, like a nonlinear conjugate gradient iteration, such strategies are often unstable, inefficient, or both. Moreover, much effort is spent estimating the nuisance variable, f, which is often subsequently discarded. Alternatively, because J(f,ϕ) is quadratic with respect to f, a closed-form expression for the minimizing value of this variable, as a function of ϕ, exists and can be used to marginalize out this variable from the cost functional.

This approach can be referred to as the variable projection ("VARPRO") strategy for separable nonlinear least squares problems. Specifically, for Eqn. (8), the optimizing expression for f is:

$$f=G^\dagger(\phi)g \quad (9);$$

where $(.)^\dagger$ denotes the left pseudo-inverse operator. Plugging this expression back into Eqn. (8) yields the following:

$$J(\phi)=P(\phi)+\|H(\phi)g\|_F^2 \quad (10);$$

where, $$H(\phi)=I-G(\phi)G^\dagger(\phi) \quad (11).$$

For many quantitative problems, P(ϕ) is a convex Markov penalty. In such cases, the single-variable problem in Eqn. (10) can be approximately minimized using discrete optimization strategies, such as graph cut techniques. For the general quantitative MRI problem, A is not the identity operator and VARPRO unfortunately cannot be used directly. As will be described, however, f can still be marginalized out of the estimation problem by constructing a specific alternating direction method of multipliers ("ADMM") paradigm.

It is noted that VARPRO cannot be easily used for the general problem in Eqn. (7) because of the action of A on G(ϕ). If these two functions can be separated, then a VARPRO-like operation can potentially be applied to the sub-problem involving only G(ϕ). To this end, instead of jointly minimizing Eqn. (7) over f and ϕ, the following equivalent constrained optimization problem can be considered:

$$[\hat{f},\hat{\phi},\hat{u},\hat{v}]=\arg\min_{f,\phi,u,v} J_{ext}(f,\phi,u,v) \quad (12)$$

such that $$u=v=G(\phi)f;$$

where u and v are "dummy" variables and the extended cost functional is:

$$J_{ext}(f,\phi,u,v)=P(\phi)+\|Au-g\|_F^2 \quad (13).$$

Although standard ADMM uses only a single operator splitting, here a second level of splitting is employed. This second level of splitting allows the preemptive decoupling between A and G (ϕ) during the VARPRO step. In other words, knowing that a step backwards will eventually be taken, two steps forward are taken up front so as to ensure that the algorithm is still only one step ahead in the end. The augmented Lagrangian ("AL") functional for Eqn. (12) is:

$$J_{AL}(f,\phi,u,v,\eta_u,\eta_v)=P(\phi)+\|Au-g\|_F^2+\mu_u\|u-v-\eta_u\|_F^2+\mu_v\|v-G(\phi)f-\eta_v\|_F^2 \quad (14);$$

with $\mu_u,\mu_v>0$, and wherein $\eta_u$ and $\eta_v$ are Lagrange multiplier vectors. An advantage of this relaxation is that only G(ϕ) acts on f, and it can now be marginalized out using VARPRO, $$J_{AL}(\phi,u,v,\eta_u,\eta_v)=P(\phi)+\|Au-g\|_F^2+\mu_u\|u-v-\eta_v\|H(\phi)(v-\eta_v)\|_F^2 \quad (15).$$

This problem can now be approached using an ADMM technique, which entails alternating minimization of J over u, v, and ϕ.

$J_{AL}$ is quadratic with respect to u, and so the minimizing value can be found by solving the following linear system:

$$\nabla_u J_{AL}=A^*(A\hat{u}-g)+\mu_u(\hat{u}-v-\eta_u)=0 \quad (16)$$

⇓

$$\hat{u}=[A^*A+\mu_u I]^{-1}[A^*g+\mu_u(v+\eta_u)].$$

In many cases, A is diagonalizable (e.g., via FFT) and so this problem can be readily solved. In non-ideal cases, such as in non-Cartesian sampling patters when using MRI data, this positive-definite linear system can be solved via conjugate gradient ("CG") iteration. Thus, at decision block 208, a check is made against a threshold, which may be a boundary condition or optimization criteria. As for the base case of A being equal to the identity operator, approximate (i.e., inexact) minimization of $J_{AL}$ with respect to ϕ can be achieved using a discrete optimization method like graph cuts. Since f is defined as a function of ϕ in this setup, it is also implicitly regularized by constraints imposed onto ϕ. This leaves only the estimation of v. Like u, v can be determined by solving the linear system corresponding to $\nabla_v J_{AL}=0$:

$$\hat{v}=\left[H^*(\phi)H(\phi)+\frac{\mu_u}{\mu_v}I\right]^{-1}\left[H^*(\phi)H(\phi)\eta_v+\frac{\mu_u}{\mu_v}(u-\eta_u)\right]; \quad (17)$$

which can be stated equivalently as:

$$\hat{v} = \left[H(\phi) + \frac{\mu_u}{\mu_v}I\right]^{-1}\left[H(\phi)\eta_v + \frac{\mu_u}{\mu_v}(u - \eta_u)\right]; \quad (18)$$

because $H(\phi)$ is both self-adjoint and idempotent. The complexity of this problem is determined by the inversion of:

$$[H(\phi) + (\gamma - 1)I]^{-1} = [\gamma I - G(\phi)[G^*(\phi)G(\phi)]^{-1}G^*(\phi)]; \quad (19)$$

where:

$$\gamma = \left(1 + \frac{\mu_u}{\mu_v}\right). \quad (20)$$

However, Woodbury's matrix identity asserts that:

$$[H(\phi) + (\gamma - 1)I]^{-1} = \gamma^{-1}\left[\left(\frac{\gamma}{\gamma - 1}\right)I - \left(\frac{1}{\gamma - 1}\right)H(\phi)\right]; \quad (21)$$

which does not contain an outer matrix inverse. Moreover, the matrix implicitly inverted inside of $H(\phi)$ is diagonal and, thus, also trivially handled. Therefore, v can also be easily estimated.

Putting all of these pieces together in the ADMM framework yields the following iterative scheme:

```
input: g , maxIter ;
define: k = 0, v = G(0)f , u = v , φ = 0, η_u = 0, η_v = 0, μ_u > 0, μ_v > 0;
repeat
  | u = [A*A + μ_u I]^{-1} [A*g + μ_u (v + η_u)];
  | v = γ^{-1}[(γ/(γ-1))I - (1/(γ-1))H(φ)][H(φ)η_v + (μ_u/μ_v)(u - η_u)];
  | φ = arg min{P(φ) + μ_v ||H(φ)(v - η_v)||_F^2};
  | η_u = η_u - (u - v);
  | η_v = η_v - (v - G(φ)f);
  | k = k + 1 k
until k ≥ maxIter ;
```

A review of the framework provided above reveals that it is of the classic ADMM form, where at each iteration a succession of independent variable estimations are performed followed by updating of the Lagrange multiplier vectors.

By using the multi-stage splitting approach described above, the large-scale system operator, A, and the nonlinear signal model functional, H (φ), are actively decoupled and, thus, have no complex interactions. Moreover, the third sub-problem of the iterative routine is similar to the classic, non-accelerated NLLS problem for which robust and efficient computational routines already exist.

Once the iterative process is completed such that the threshold at decision block 208 is met, at process block 210 the quantitative estimates can be registered with anatomical information from the data acquired at process block 202 or other anatomical information. At process block 212, a report is communicated, for example, as a set of images with registered quantitative estimates coupled with anatomical images. For example, the quantitative estimates may be overlaid on anatomical images, such as using a color coding or other display or report mechanism.

Thus, the present disclosure may utilize a specific ADMM strategy, which is a form of augmented Lagrangian routine, to actively decouple the challenging components of an estimation model so they can be focused on independently. More specifically, the ADMM strategy makes use of a multi-level splitting routine that prospectively enables the use of a dimensionality reduction strategy called variable projection ("VARPRO"). This approach greatly reduces the overall complexity of the estimation problem while simultaneously providing a pathway to circumvent mathematical challenges associated with non-uniqueness problems, like phase wrapping.

The present disclosure includes discussion of one or more preferred embodiments, and it should be appreciated that many equivalents, alternatives, variations, and modifications, aside from those expressly stated, are possible and within the scope of the invention.

The invention claimed is:

1. A system for generating medical images comprising:
  a communications connection configured to receive image data acquired from a subject using a medical imaging system;
  a processor configured to receive the image data and to:
    a) estimate a physiological parameter from the image data by inputting the image data to an estimation model comprising a model of the medical imaging system that is decoupled from a physics-based model of the image data, generating output as the estimate of the physiological parameter, wherein the physics-based model comprises a nonlinear signal model functional that models the image data such that the image data have a nonlinear dependence on at least one parameter of the physics-based signal model, and the model of the medical imaging system is actively decoupled from the physics-based model by applying a multi-level splitting routine to the model of the medical imaging system and the physics-based model;
    b) iteratively minimize a cost function that includes the model of the medical imaging system and the physics-based model of the acquired data to quantify the physiological parameter of the subject from the image data; and
    c) reconstruct a set of medical images of the subject from the image data at least including the physiological parameter of the subject.

2. The system of claim 1 wherein the model of the medical imaging system is a large-scale system operator that describes data acquisition using the medical imaging system.

3. The system of claim 2 wherein the medical imaging system is a magnetic resonance imaging (MRI) system and the model of the medical imaging system includes a Fourier transform.

4. The system of claim 1 wherein to estimate the physiological parameter the processor is further caused to apply the multi-level splitting routine in order to prospectively enable the use of a dimensionality reduction strategy to reduce overall complexity of the estimation due to non-uniqueness of data.

5. The system of claim 1 wherein to estimate the physiological parameter the processor is further caused to form separable nonlinear least squares problems.

6. The system of claim 1 wherein to iteratively minimize the cost function, the processor is further caused to control an influence of ancillary parameters, f, that are not associated with the physiological parameter.

7. The system of claim 6 wherein to control an influence of ancillary parameters, f, the processor is further caused to marginalize f out of estimations by constructing a specific alternating direction method of multipliers ("ADMM") paradigm.

8. The system of claim 7 wherein to iteratively minimize the cost function, the processor is further caused to solve a linear system of:

$$\nabla_u J_{AL} = A^*(A\hat{u} - g) + \mu_u(\hat{u} - v - \eta_u) = 0$$
$$\Downarrow$$
$$\hat{u} = [A^*A + \mu_u I]^{-1}[A^*g + \mu_u(v + \eta_u)]$$

where $J_{AL}$ is quadratic with respect to $\mu$, A is the system model, g is the image data, u and v are "dummy" variables that extended cost functions, $\mu_u, \mu_v > 0$, and wherein $\eta_u$ and $\eta_v$ are Lagrange multiplier vectors.

9. The system of claim 2 wherein the medical imaging system is a magnetic resonance imaging (MRI) system and the physics-based model includes a magnetic resonance signal model.

10. A method for estimating a physiological parameter from data acquired with a medical imaging system, the steps of the method comprising:
  a) acquiring data with the medical imaging system;
  b) estimating a physiological parameter from the acquired data by inputting the acquired data to an estimation model comprising a model of the medical imaging system that is decoupled from a physics-based model of the acquired data, generating output as the estimate of the physiological parameter, wherein the physics-based model comprises a nonlinear signal model functional that models the acquired data such that the acquired data have a nonlinear dependence on at least one parameter of the physics-based signal model, and the model of the medical imaging system is actively decoupled from the physics-based model by applying a multi-level splitting routine to the model of the medical imaging system and the physics-based model; and
  c) reconstructing a set of medical images from the data, the medical images at least including the physiological parameter.

11. The method as recited in claim 10 wherein step b) includes iteratively minimizing a cost function that includes the model of the medical imaging system and the physics-based model of the acquired data.

12. The method as recited in claim 11 wherein step b) includes marginalizing unwanted variables out of the cost functional.

13. The method as recited in claim 12 wherein step b) in which one level of the multi-level splitting routine includes decoupling the model of the medical imaging system from the physics-based model of the acquired data.

14. The method as recited in claim 10 wherein step b) includes using an alternating direction method of multipliers routine to decouple the model of the medical imaging system from the physics-based model of the acquired data.

15. The method as recited in claim 10 wherein the medical imaging system is a magnetic resonance imaging (MRI) system, the model of the medical imaging system includes a Fourier transform, and the physics-based model of the acquired data is a magnetic resonance signal model.

16. A magnetic resonance imaging (MRI) system, comprising:
  a magnet system configured to generate a polarizing magnetic field about at least a portion of a subject arranged in the MRI system;
  a magnetic gradient system including a plurality of magnetic gradient coils configured to apply at least one magnetic gradient field to the polarizing magnetic field;
  a radio frequency (RF) system configured to apply an RF field to the subject and to receive magnetic resonance signals from the subject using a coil array;
  a computer system processor programmed to:
    control the magnetic gradient system and the RF system to acquire image data;
    estimate a physiological parameter from the image data by inputting the image data to an estimation model comprising a model of the MRI system that is decoupled from a physics-based model of the image data, generating output as the estimate of the physiological parameter, wherein the physics-based model comprises a nonlinear signal model functional that models the image data such that the image data have a nonlinear dependence on at least one parameter of the physics-based signal model, and the model of the medical imaging system is actively decoupled from the physics-based model by applying a multi-level splitting routine to the model of the medical imaging system and the physics-based model;
    and
    generate a quantitative image of the subject with the physiological parameter.

17. The MRI system of claim 16 wherein to estimate the physiological parameter the processor is further caused to apply the multi-level splitting routine in order to prospectively enable the use of a dimensionality reduction strategy to reduce overall complexity of the estimation due to non-uniqueness of data.

18. The MRI system of claim 16 wherein to estimate the physiological parameter the processor is further caused to form separable nonlinear least squares problems.

19. The MRI system of claim 16, further comprising iteratively minimizing a cost function, the processor programmed to control an influence of ancillary parameters, f, that are not associated with the physiological parameter.

20. The MRI system of claim 19 wherein to control an influence of ancillary parameters, f, the processor is further caused to marginalize f out of estimations by constructing a specific alternating direction method of multipliers ("ADMM") paradigm.

\* \* \* \* \*